United States Patent
Raheem et al.

(10) Patent No.: US 11,220,500 B2
(45) Date of Patent: Jan. 11, 2022

(54) CRYSTALLINE FORM OF VALBENAZINE DIBESYLATE

(71) Applicant: Apotex Inc., Toronto (CA)

(72) Inventors: Mohammed Abdul Raheem, Brantford (CA); Yajun Zhao, Brantford (CA); Minh T. N. Nguyen, St. George (CA); Mohamed Ibrahim Zaki, Brantford (CA); Jenny L. Gerster, Brantford (CA); Stuart P. Green, Mount Pleasant (CA); Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 16/718,841

(22) Filed: Dec. 18, 2019

(65) Prior Publication Data
US 2020/0207761 A1 Jul. 2, 2020

Related U.S. Application Data

(60) Provisional application No. 62/785,371, filed on Dec. 27, 2018.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................................................. C07D 471/04
USPC ....................................................... 546/101
See application file for complete search history.

(56) References Cited

U.S. PATENT DOCUMENTS

| 8,039,627 B2 | 10/2011 | Gano |
| 10,065,952 B2 * | 9/2018 | McGee ................ C07D 471/04 |
| 10,160,757 B2 | 12/2018 | McGee et al. |

FOREIGN PATENT DOCUMENTS

| WO | 2008058261 A1 | 5/2008 |
| WO | 2017075340 A1 | 5/2017 |
| WO | 2017112857 A1 | 6/2017 |
| WO | 2018067945 A1 | 4/2018 |
| WO | 2018153632 A1 | 8/2018 |

OTHER PUBLICATIONS

Porter, "Coating of Pharmaceutical Dosage Forms", Remington: The Science and Practice of Pharmacy, 2006, Chapter 46, pp. 929-938, 21st Edition, Lippincott Williams & Wilkins, Philadelphia, USA.
Bernstein, "Is This Material Polymorphic?", Polymorphism in Molecular Crystals, 2002, pp. 9-10, Clarendon Press, Oxford, United Kingdom.
Ding et al., "Extended-Release and Targeted Drug Delivery Systems", Remington The Science and Practice of Pharmacy, 2006, pp. 939-964, 21st Edition, Lippincott, Williams & Wilkins, Philadelphia, United States.
Rudnic et al., "Oral Solid Dosage Forms", Remington The Science and Practice of Pharmacy, 2006, pp. 889-928, 21st Edition, Lippincott, Williams & Wilkins, Philadelphia, United States.

* cited by examiner

*Primary Examiner* — Nizal S Chandrakumar
(74) *Attorney, Agent, or Firm* — The Webb Law Firm

(57) ABSTRACT

The present invention provides a novel crystalline form of Valbenazine dibesylate, Valbenazine dibesylate Form APO-I, compositions and processes for the preparation thereof, and the use of this crystalline form in the treatment of hyperkinetic disorders, including tardive dyskinesia.

18 Claims, 2 Drawing Sheets

CRYSTALLINE FORM OF VALBENAZINE DIBESYLATE

CROSS-REFERENCE TO RELATED APPLICATION

This application claims priority to U.S. Provisional Patent Application No. 62/785,371 filed Dec. 27, 2018, the disclosure of which is hereby incorporated by reference in its entirety.

TECHNICAL FIELD

The present invention is directed to a novel crystalline form of Valbenazine dibesylate, pharmaceutical compositions containing this form, processes for its preparation, and its use in the treatment of hyperkinetic disorders, including tardive dyskinesia.

BACKGROUND

Valbenazine (1), or (2R,3R,11bR)-1,3,4,6,7,11b-hexahydro-9,10-dimethoxy-3-(2-methylpropyl)-2H-benzo[a]quinolizin-2-yl-L-valine ester, in the form of a ditosylate salt, is the active pharmaceutical ingredient in INGREZZA™, which is indicated for the treatment of tardive dyskinesia.

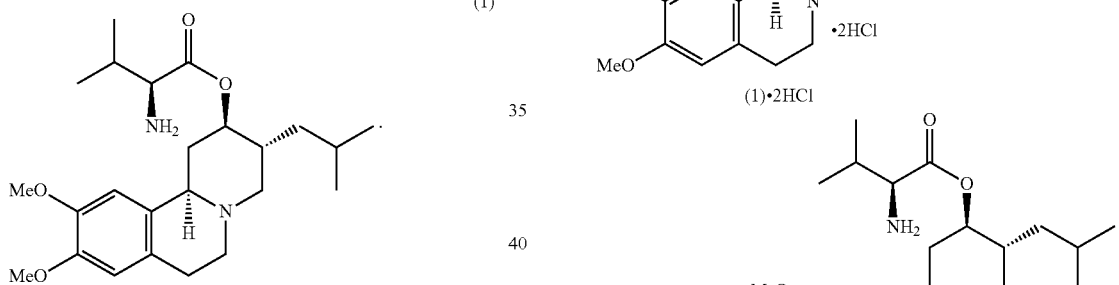

(1)

Valbenazine (1) is disclosed in WO 2008/058261 A1 as one compound in a group of tricyclic compounds exhibiting inhibition of the vesicular monoamine transporter 2 (VMAT2). Various Valbenazine salts, and crystalline forms thereof, are disclosed in WO 2017/075340 A1, WO 2017/112857 A1, WO 2018/067945 A1 and WO 2018153632 A1.

For example, WO 2017/075340 A1 discloses the results of counterion screening involving treatment of Valbenazine with 18 different acids to form salts, including the marketed salt form, Valbenazine ditosylate, and Valbenazine dibesylate, among others.

WO 2017/112857 A1 describes a method for the preparation of Valbenazine ditosylate utilizing Valbenazine dihydrochloride salt as an intermediate (see Scheme 1). In this preparation, the compound of Formula (A) is coupled with t-butoxycarbonyl (BOC)-protected L-valine to provide the compound of Formula (B), which is deprotected with hydrogen chloride to provide Valbenazine (1) as a dihydrochloride salt. The dihydrochloride salt is converted to Valbenazine ditosylate by liberation of Valbenazine (1) using a base, followed by treatment with p-toluenesulfonic acid monohydrate. However, this approach for the preparation of Valbenazine ditosylate, which requires the formation of an intermediate dihydrochloride salt, is inefficient.

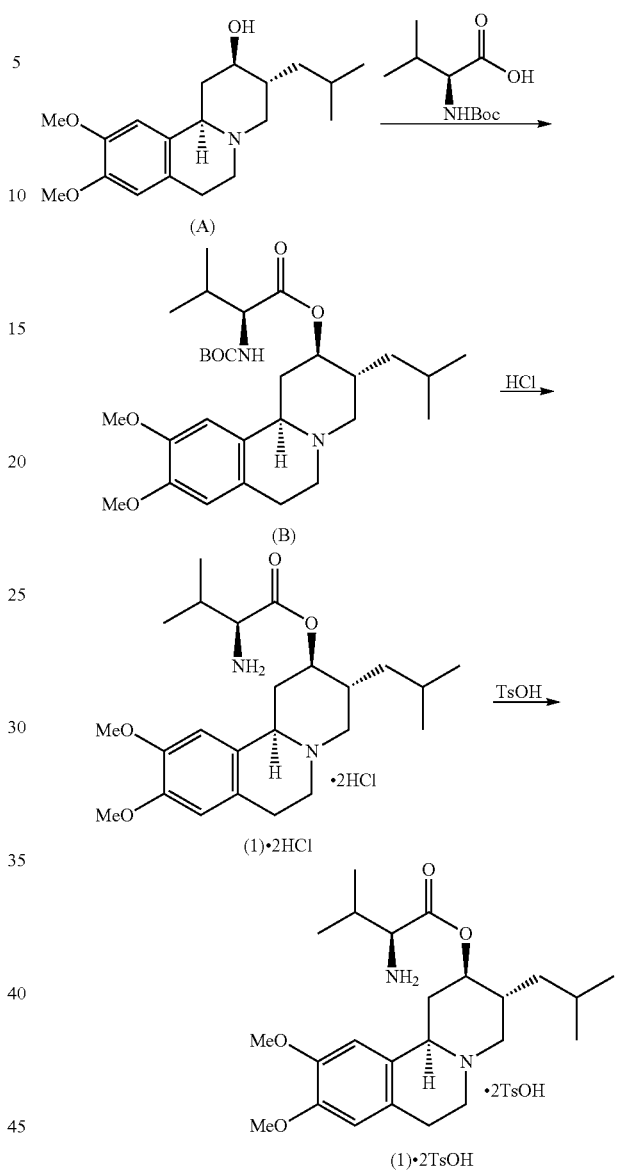

Scheme 1 (Prior Art)

In WO 2018/067945 A1, Valbenazine salts and crystalline forms thereof with the following acids are disclosed, including the p-toluenesulfonate, fumarate, stearate, palmitate, sulfate and methanesulfonate salts. These salts and crystalline forms are reported to be suitable for use in pharmaceutical compositions and medical treatments. The ditosylate salt of WO 2018/067945 A1 is prepared by treatment of the same BOC-protected compound of Formula (B) shown in Scheme 1 with p-toluenesulfonic acid monohydrate, rather than hydrogen chloride, to effect deprotection and salt formation.

In WO 2018/153632 A1, Valbenazine ditosylate, dihydrochloride and crystalline forms thereof are disclosed, as well as pharmaceutical compositions and uses thereof in the treatment of movement disorders. The Valbenazine salts are prepared by treatment of Valbenazine free base form with the corresponding acid.

Numerous salts of Valbenazine have been disclosed, many of which are reported to be suitable for incorporation into pharmaceutical compositions and for use in the treatment of movement disorders, including tardive dyskinesia. In particular, reports of the suitability of the Valbenazine ditosylate salt and the Valbenazine dihydrochloride salt are more prevalent than other Valbenazine salts. However, both the ditosylate salt and the dihydrochloride salt of Valbenazine are reported to exist in multiple crystalline forms, several of which are reported to undergo form conversion depending on the levels of atmospheric humidity. The tendency of the known crystalline forms to undergo form conversion following exposure to moisture limits their usefulness in commercial products since it requires specialised practices to avoid conversion during drying, handling, storage, and formulation activities.

Furthermore, many methods reported for the preparation of Valbenazine salts and crystalline forms thereof are inefficient, comprising either a) treatment of Valbenazine free base form, obtained by deprotection of a synthetic precursor, with the corresponding acid, or b) conversion of a first salt, obtained by deprotection of a synthetic precursor with a first acid, to a second salt by treatment with a second acid.

Different crystalline forms of the same compound may have different crystal packing, thermodynamic, spectroscopic, kinetic, surface and mechanical properties. For example, different crystalline forms may have different stability properties such that a particular crystalline form may be less sensitive to heat, relative humidity (RH) and/or light. Different crystalline forms of a compound may also be more susceptible to moisture uptake, resulting in a potential alteration of physical characteristics of the form such as flowability, density or compressibility, which can lead to problems during formulation/tabletting and/or to changes in dissolution rate of the formulated drug product. For example, unintended absorption of moisture by a hygroscopic crystalline form of a drug substance can alter its compressibility during tabletting, resulting in a softer tablet having a faster dissolution rate following administration. A particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Such properties may provide for more suitable product qualities, including a dosage form that is more resistant to discolouration when comprised of a specific crystalline form. Particular crystalline forms may also have different solubilities, thereby providing different pharmacokinetic parameters, which allow for specific crystalline forms to be used in order to achieve specific pharmacokinetic targets.

Although general approaches to crystalline form screening of active pharmaceutical ingredients are known, it is well established that the prediction of whether any given compound or salt will exhibit polymorphism is not possible. Accordingly, it is not possible to extend generalities to the number and kinds of crystalline forms that can exist for Valbenazine salts, or to what methods will be suitable for the preparation of any given crystalline form. Furthermore, prediction of the properties of any unknown crystalline forms, and how they will differ from other crystalline forms of the same compound or salt, remains elusive (Joel Bernstein, *Polymorphism in Molecular Crystals*).

There exists a need for novel forms of Valbenazine in the form of salts and crystalline forms thereof having improved properties for use in providing drug products comprising Valbenazine, and commercially amenable processes for their manufacture.

SUMMARY OF THE INVENTION

The present invention provides a crystalline form of a Valbenazine salt having 1 mole of Valbenazine and approximately 2 moles of benzenesulfonic acid, referred to herein as Valbenazine dibesylate'. Benzenesulfonate is a pharmaceutically acceptable counterion having toxicological acceptability similar to p-toluenesulfonate, the counterion used in the Valbenazine ditosylate drug product INGREZZA™, which has a proven safety and efficacy record evidenced by its regulatory approval by the U.S. Food & Drug Administration. The Valbenazine dibesylate crystalline form of the present invention also has aqueous solubility across a range of pH values that is comparable to the Valbenazine ditosylate in the drug product. Furthermore, the Valbenazine dibesylate crystalline form of the present invention exhibits form stability when stored for prolonged periods of time at moderate temperatures and humidity. Each of these factors is expected to support the suitability of the Valbenazine dibesylate crystalline form of the present invention as a safe and effective alternative to the Valbenazine ditosylate salt used in the approved drug product.

Furthermore, the present invention provides a crystalline form of Valbenazine dibesylate that can be prepared by an efficient and industrially compatible process. The Valbenazine dibesylate crystalline form of the present invention can be prepared in high yield and purity directly from a synthetic precursor bearing an acid-labile protecting group by treatment with benzenesulfonic acid. Surprisingly, substituting p-toluenesulfonic acid for benzenesulfonic acid in the same process results in higher levels of a hydrolysis impurity, the removal of which lowers the efficiency of the process. Thus, the crystalline Valbenazine dibesylate form of the present invention provides advantages in terms of industrial efficiency.

Accordingly, in a first aspect of the present invention, there is provided a crystalline form of Valbenazine dibesylate, APO-I, characterized by a PXRD diffractogram comprising peaks, expressed in degrees 2θ (±0.2°), at 6.3°, 9.8° and 15.6°. In a preferred embodiment of the first aspect, the PXRD diffractogram further comprises at least three peaks, expressed in degrees 2θ (±0.2°), selected from the group consisting of: 5.3°, 7.7°, 8.5°, 12.5°, 14.0°, 16.8°, 17.1°, 17.8°, 18.6° and 19.7°. In a further preferred embodiment of the first aspect, the PXRD diffractogram further comprises peaks, expressed in degrees 2θ (±0.2°), at 5.3°, 7.7°, 8.5°, 12.5°, 14.0°, 16.8°, 17.1°, 17.8°, 18.6° and 19.7°. Preferably, the crystalline form of the first aspect of the invention provides a PXRD diffractogram comprising peaks in substantially the same positions (±0.2° 2θ) as those shown in FIG. 1. In another preferred embodiment of the first aspect, the crystalline form is characterized by a DSC thermogram comprising an endothermic peak with a peak onset at approximately 235° C. and a peak maximum at approximately 238° C. More preferably, the DSC thermogram is substantially the same in appearance as the DSC thermogram provided in FIG. 2.

In a second aspect of the present invention, there is provided a pharmaceutical composition comprising a crystalline form of Valbenazine dibesylate according to the first aspect of the invention, and one or more pharmaceutically acceptable excipients. Preferably, the pharmaceutical composition is in the form of a solid dosage form. Most preferably, the pharmaceutical composition is a capsule. In a preferred embodiment of the second aspect, the pharmaceutical composition comprises an amount of the crystalline form of the first aspect of the invention that is equivalent to 40 mg or 80 mg Valbenazine free base.

In a third aspect of the present invention, there is provided a use of a crystalline form of Valbenazine dibesylate according to the first aspect of the invention, or the pharmaceutical composition of the second aspect of the invention, in the treatment of a hyperkinetic disorder. In a preferred embodiment of the third aspect, the hyperkinetic disorder is Huntington's disease, tardive dyskinesia, Tourette's syndrome or tics. Most preferably, the hyperkinetic disorder is tardive dyskinesia.

In a fourth aspect of the present invention, there is provided a process for the preparation of Valbenazine dibesylate Form APO-I, ((1).2BsOH):

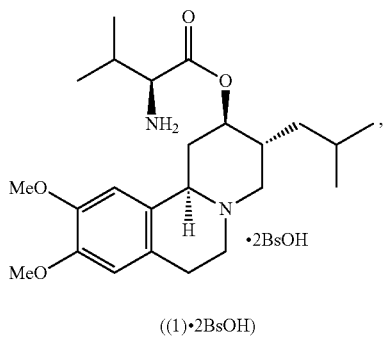

((1)·2BsOH)

the process comprising:
(i) reacting, in the presence of a first solvent (S1), a compound of Formula (2):

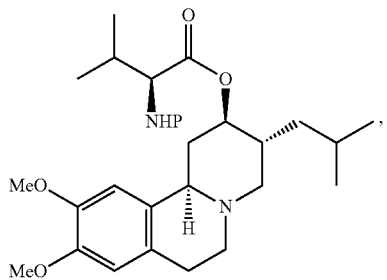

with at least two equivalents of benzenesulfonic acid (BsOH) to afford Valbenazine dibesylate;
(ii) forming a suspension of Valbenazine dibesylate; and
(iii) filtering the suspension to isolate the Valbenazine dibesylate Form APO-I,
wherein P is an acid-labile protecting group.

In a preferred embodiment of the fourth aspect, P is selected from the group consisting of substituted or unsubstituted alkyloxycarbonyl, aryloxycarbonyl, arylalkyloxycarbonyl, alkylcarbonyl and arylcarbonyl groups. Preferably, P is tert-butoxycarbonyl (BOC). In another preferred embodiment of the fourth aspect, the first solvent (S1) is selected from the group consisting of nitriles and halogenated hydrocarbons. Preferably, the first solvent (S1) is acetonitrile or dichloromethane. In a further preferred embodiment of the fourth aspect, the suspension of Valbenazine dibesylate is formed by the addition of a second solvent (S2), preferably butanone. In another preferred embodiment of the fourth aspect, the first solvent (S1) is partially or wholly removed prior to addition of the second solvent (S2).

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

The Valbenazine dibesylate crystalline form of the present invention comprises the benzenesulfonate counterion, a widely accepted toxicological surrogate of p-toluenesulfonic acid. As such, the Valbenazine dibesylate crystalline form of the present invention is expected to have toxicological acceptability comparable to the Valbenazine ditosylate salt in the approved drug product. Also of importance is that the crystalline form of the present invention has aqueous solubility across a pH range of 1.2 to 6.8 that is within 10% units (expressed as mg/mL Valbenazine free base) of that of the Valbenazine ditosylate incorporated into the approved drug product. Additionally, the crystalline form of the present invention exhibits form stability following open exposure to conditions of 27° C./60% RH for at least 5 months. All of these factors weigh favourably towards establishing pharmaceutical equivalency between Valbenazine ditosylate and the Valbenazine dibesylate crystalline form of the present invention. Accordingly, it is expected that demonstrating safety and efficacy of the Valbenazine dibesylate crystalline form of the present invention by comparison to previously approved Valbenazine ditosylate should be simplified in comparison to other Valbenazine salts having less closely aligned physico-chemical properties.

Furthermore, the present invention provides a crystalline form of Valbenazine dibesylate that can be prepared in high yield and purity by an efficient and industrially compatible process. As shown in Scheme 2, treatment of a compound of Formula (2), bearing an acid-labile protecting group such as t-butoxycarbonyl (BOC), with benzenesulfonic acid affords the Valbenazine dibesylate salt directly rather than in a two-step approach proceeding through a further intermediate salt as disclosed in, for example, WO 2017/112857 A1. Surprisingly, despite the structural similarities between p-toluenesulfonic acid and benzenesulfonic acid, the Valbenazine dibesylate crystalline form of the present invention can be prepared in this direct manner in high yield and purity, whereas the corresponding Valbenazine ditosylate salt prepared using the same approach contains higher levels of a hydrolysis impurity.

Scheme 2

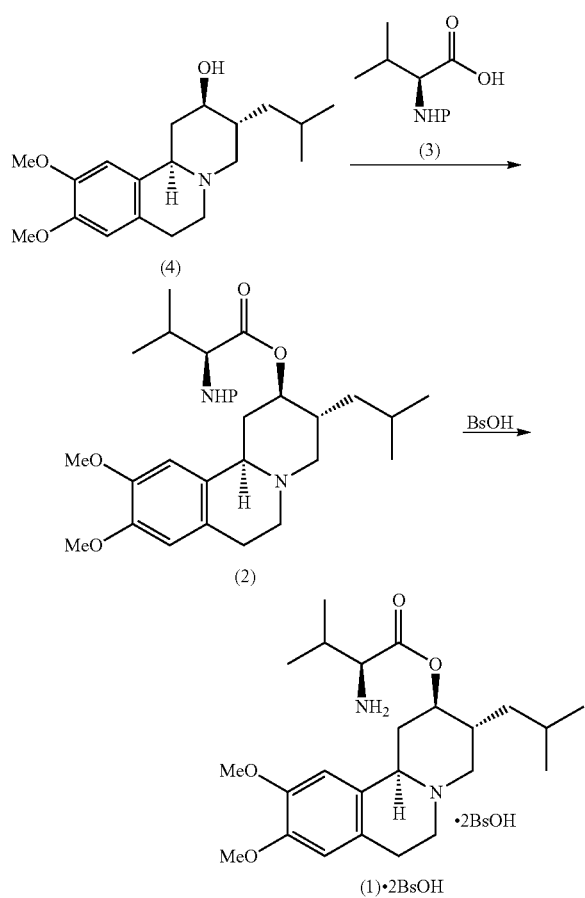

wherein P is an acid-labile protecting group.

The Valbenazine dibesylate crystalline form of the present invention exhibits differences in properties when compared to the known Valbenazine salts. Properties that differ between the invention and known Valbenazine salts include crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tabletting, handling, flow, and blending.

Figure 1:
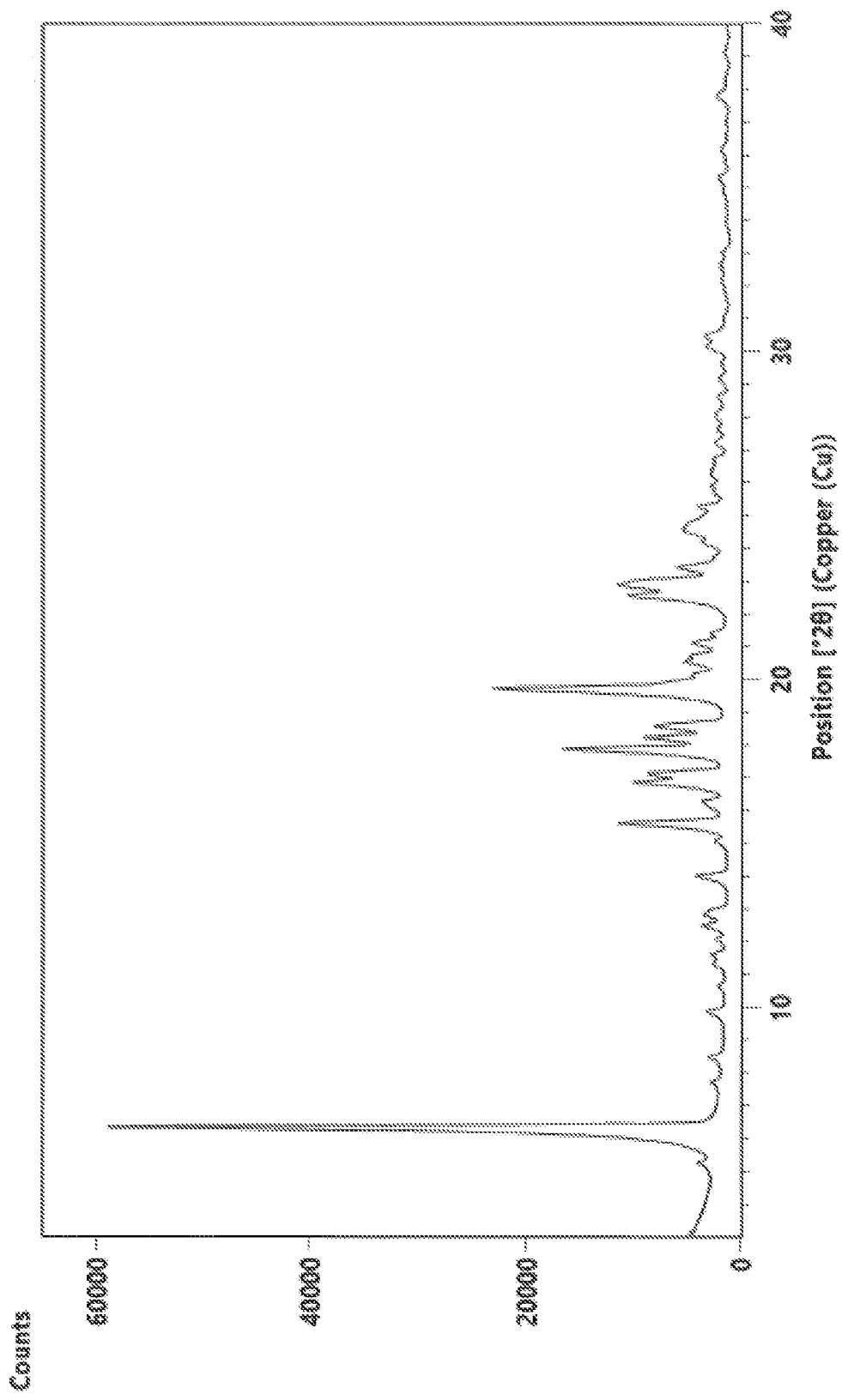
FIG. 1 is a representative PXRD diffractogram of Valbenazine dibesylate Form APO-I as prepared in Example 1.

Depending on the manner in which the crystalline forms of the present invention are prepared, and the methodology and instrument used for PXRD analysis, the intensity of a given peak observed in a PXRD diffractogram of the crystalline form may vary when compared to the same peak in the representative PXRD diffractogram provided in FIG. 1. Thus, differences in relative peak intensities between peaks in a PXRD diffractogram for a given crystalline form may be observed when compared to the relative peak intensities of the peaks in the representative PXRD diffractogram of FIG. 1. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIG. 1, it is understood that individual peak positions may vary between ±0.2° 2θ from the values observed in the representative PXRD diffractograms provided in FIG. 1 for the crystalline form of the invention, or listed in Table 1. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractogram provided in FIG. 1. Thus, PXRD diffractograms of the crystalline form of the present invention may, in some circumstances, display the same relative peak positions as observed in the representative PXRD diffractogram provided in FIG. 1, with the exception that each peak is offset in the same direction, and by approximately the same amount, such that the overall PXRD diffractogram is substantially the same in appearance as the PXRD diffractogram of FIG. 1, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractogram of FIG. 1.

Figure 2:
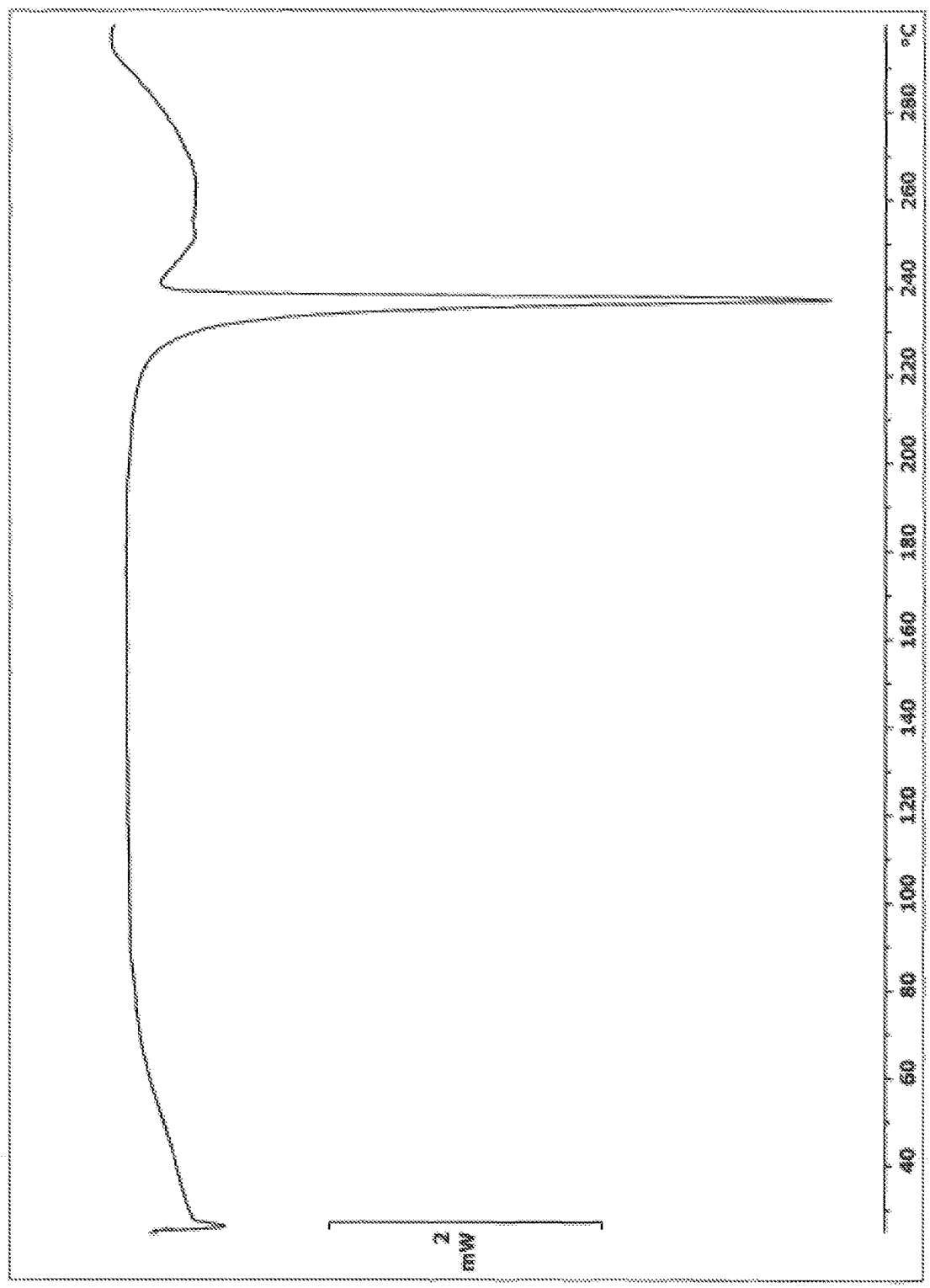
FIG. 2 is a representative DSC thermogram of Valbenazine dibesylate Form APO-I as prepared in Example 1.

Depending on the manner in which the crystalline forms are prepared, the methodology and instrument used for DSC analysis, it is understood that peaks corresponding with thermal events in a DSC thermogram may vary between ±2° C. from the values observed in the representative DSC thermogram provided in FIG. 2 and described herein. Such variations are known and understood by a person of skill in the art, and any such variations do not depart from the invention disclosed herein.

As used herein, the term 'crystalline form' refers to a substance with a particular arrangement of molecular components in its crystal lattice, and which may be identified by physical characterization methods such as PXRD.

As used herein, the term "room temperature" refers to a temperature in the range of 20° C. to 25° C.

As used herein, the term "alkyl", alone or as part of another substituent, means, unless otherwise stated, a straight or branched chain, saturated hydrocarbon radical having 1 to 10 carbon atoms. Preferred alkyl groups include methyl, ethyl, n-propyl, iso-propyl, n-butyl, t-butyl, iso-butyl, sec-butyl, n-pentyl, 2,2-dimethylpropyl, n-hexyl, 2-methylpentyl, n-heptyl, n-octyl, 2-methylheptyl, 3-methylheptyl, n-nonyl, 2-methyloctyl and n-decyl. Particularly preferred alkyl groups are methyl, ethyl, n-propyl, iso-propyl, n-butyl, t-butyl, iso-butyl and sec-butyl.

As used herein, the term "aryl", alone or as part of another substituent, means a polyunsaturated, aromatic, hydrocarbon radical which can comprise one, two or three rings, which are fused together or linked covalently, having a total of 6 to 14 ring carbon atoms. Preferred aryl groups include phenyl, 4-biphenyl, 9-fluorenyl and 9-anthryl. Particularly preferred aryl groups are phenyl and 9-anthryl.

As used herein, the term "arylalkyl", alone or as part of another substituent, means an aryl substituent attached through an alkyl radical to the parent structure, wherein the aryl portion has from 6 to 10 ring carbons, and the alkyl portion has from 1 to 3 carbons in the alkyl portion. Preferred arylalkyl groups include 1-methyl-1-phenylethyl, 1-methyl-1-(4-biphenylyl)ethyl, benzyl, 9-fluorenylmethyl and phenethyl. Particularly preferred arylalkyl groups are benzyl, 9-fluorenylmethyl and phenethyl.

As used herein, the term "substituted" refers to the replacement of one or more hydrogen atoms in an alkyl, aryl or arylalkyl group with a substituent selected from the group consisting of: halogen, R' and $NO_2$. Each R' may be selected, independently, from the group consisting of alkyl groups, aryl groups and arylalkyl groups as defined herein. Preferred substituent groups on substituted alkyl, aryl and arylalkyl groups are methyl, nitro, fluoride and chloride.

As used herein, the term TsOH refers to p-toluenesulfonic acid.

As used herein, the term BsOH refers to benzenesulfonic acid.

In one embodiment of the present invention, there is provided a new crystalline form of Valbenazine dibesylate, Valbenazine dibesylate Form APO-I.

Valbenazine dibesylate Form APO-I can be characterized by a PXRD diffractogram comprising, among other peaks, characteristic peaks, expressed in degrees 2θ (±0.2°), at 6.3°, 9.8° and 15.6°. Preferably, the PXRD diffractogram further comprises at least three peaks, expressed in degrees 2θ (±0.2°), selected from the group consisting of 5.3°, 7.7°, 8.5°, 12.5°, 14.0°, 16.8°, 17.1°, 17.8°, 18.6° and 19.7°. More preferably, the PXRD diffractogram further comprises peaks, expressed in degrees 2θ (±0.2°), at 5.3°, 7.7°, 8.5°, 12.5°, 14.0°, 16.8°, 17.1°, 17.8°, 18.6° and 19.7°. PXRD studies of uncapped samples of Valbenazine dibesylate Form APO-I maintained in a 27° C./60% RH stability chamber for at least 20 weeks showed that no change in the crystalline form occurred.

An illustrative PXRD diffractogram of Valbenazine dibesylate Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the Valbenazine dibesylate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Valbenazine dibesylate Form APO-I from Figure 1

| Angle (2θ) | Relative intensity (%) |
|---|---|
| 5.26 | 2.1 |
| 6.31 | 100.0 |
| 7.70 | 1.4 |
| 8.45 | 2.1 |
| 9.83 | 2.9 |
| 12.47 | 4.0 |
| 13.97 | 5.2 |
| 15.57 | 20.9 |
| 16.82 | 15.7 |
| 17.11 | 11.8 |
| 17.82 | 27.9 |
| 18.20 | 12.3 |
| 18.55 | 11.7 |
| 19.67 | 36.6 |
| 22.52 | 14.7 |
| 22.84 | 13.5 |

An illustrative DSC thermogram of Valbenazine dibesylate Form APO-I is shown in FIG. 2. The DSC thermogram may be further characterized by an endothermic peak with a peak onset at approximately 235° C. and a peak maximum at approximately 238° C.

In another embodiment of the present invention, a process is provided for the preparation of Valbenazine dibesylate Form APO-I, ((1).2BsOH):

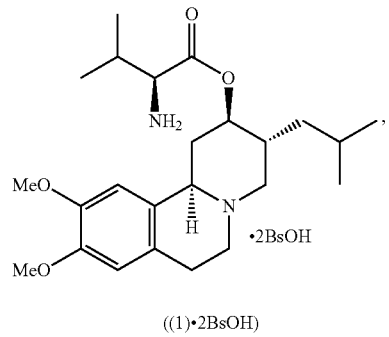

((1)·2BsOH)

the process comprising:
(i) reacting, in the presence of a first solvent (S1), a compound of Formula (2):

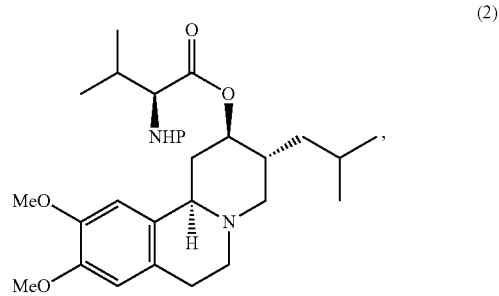

with at least two equivalents of benzenesulfonic acid (BsOH) to afford Valbenazine dibesylate;
(ii) forming a suspension of Valbenazine dibesylate; and
(iii) filtering the suspension to isolate the Valbenazine dibesylate Form APO-I,
wherein P is an acid-labile protecting group.

In the compound of Formula (2), P is an acid-labile protecting group, preferably selected from the group consisting of substituted or unsubstituted alkyloxycarbonyl groups such as methoxycarbonyl, tert-butoxycarbonyl (BOC), 2,2,2-trichloroethoxycarbonyl and 2-trimethylsilylethoxycarbonyl; substituted or unsubstituted arylalkyloxycarbonyl groups such as benzyloxycarbonyl (CBz), p-nitrobenzyloxycarbonyl and diphenylmethoxycarbonyl; substituted or unsubstituted alkylcarbonyl (Ac) groups such as methylcarbonyl and chloromethylcarbonyl; and substituted or unsubstituted arylalkylcarbonyl groups such as benzylcarbonyl (Bz). More preferably, the protecting group is tert-butoxycarbonyl (BOC) or benzyloxycarbonyl (CBz), most preferably, tert-butoxycarbonyl (BOC).

In the reaction of the compound of Formula (2) and benzenesulfonic acid, the amount of benzenesulfonic acid used is in the range of approximately 2.0 to 3.0 mole equivalents with respect to the compound of Formula (2). Preferably the amount of benzenesulfonic acid used in the reaction is in the range of approximately 2.0 to approximately 2.5 mole equivalents with respect to the compound of Formula (2).

The reaction of the compound of Formula (2) and benzenesulfonic acid is conducted in the presence of a first solvent (S1), which is inert to the reaction conditions, and is preferably selected from the group consisting of halogenated hydrocarbons and nitriles. More preferably, the solvent is selected from the group consisting of dichloromethane and acetonitrile.

The reaction of the compound of Formula (2) and benzenesulfonic acid may be conducted at any suitable temperature, and is preferably conducted at an elevated temperature in the range of approximately 35° C. to approximately 50° C.

Following the reaction of the compound of Formula (2) with benzenesulfonic acid, a second solvent (S2) can be used to induce or facilitate crystallization and formation of a suspension of Valbenazine dibesylate. The second solvent (S2) may be selected from the group consisting of acetone, butanone and 4-methylpentan-2-one. Most preferably, the second solvent (S2) is butanone. If desired, the solvent first (S1) may be removed or reduced before or after addition of the second solvent (S2) to facilitate crystallization of Valbenazine dibesylate.

As shown in Scheme 2, the compound of Formula (2) can be obtained by reaction of a compound of Formula (4) with a compound of Formula (3).

In a further embodiment of the invention, there is provided a pharmaceutical composition of a crystalline form of Valbenazine dibesylate comprising Valbenazine dibesylate with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a capsule. Preferably, the pharmaceutical composition provides a dose of Valbenazine dibesylate that is equivalent to the 40 mg or 80 mg of Valbenazine free base found in INGREZZA™ drug products.

Suitable pharmaceutically acceptable excipients are preferably inert with respect to the crystalline form of Valbenazine dibesylate of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Other suitable excipients and the preparation of solid oral dosage forms is well known to person of skill in the art, and is described generally, for example, in *Remington The Science and Practice of Pharmacy 21$^{st}$ Edition* (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in *Remington The Science and Practice of Pharmacy 21$^{st}$ Edition* (Lippincott Williams & Wilkins: Philadelphia; 2006; Chapter 46).

EXAMPLES

The following non-limiting examples are illustrative of some of the aspects and embodiments of the invention described herein.

The compound of Formula (4) used in the following examples was a monohydrate form which was dried prior to use by applying methods known in the art, including stirring in dichloromethane in the presence of molecular sieves at room temperature for a sufficient period, typically 1-2 hours, to afford a solution having a low water content by Karl Fischer (KF) analysis, typically <0.1% w/w.

PXRD Analysis:

Data were acquired on a PANanalytical X'Pert Pro MPD diffractometer with fixed divergence slits and an X'Celerator detector. The diffractometer was configured in Bragg-Brentano geometry; data was collected over a 2θ range of 3° to 40° using CuKα radiation at a power of 40 mA and 45 kV. CuKβ radiation was removed using a divergent beam nickel filter. A step size of 0.017°, and a step time of 40 seconds, was used. Raw data were evaluated using X'Pert High Score Plus. Samples were rotated to reduce preferred orientation effects. Samples were lightly ground prior to analysis.

Differential Scanning Calorimetry Analysis:

DSC thermograms were collected on a Mettler-Toledo 821e instrument. Samples (2±0.2 mg) were weighed into a 40 μL aluminum pan and were crimped closed with an aluminum lid having a 1 mm pinhole. The samples were analyzed under a flow of nitrogen (50±5 mL/min) at a scan rate of 10° C./minute between 25° C. and 300° C.

Example 1: Preparation of Valbenazine Dibesylate Form APO-I

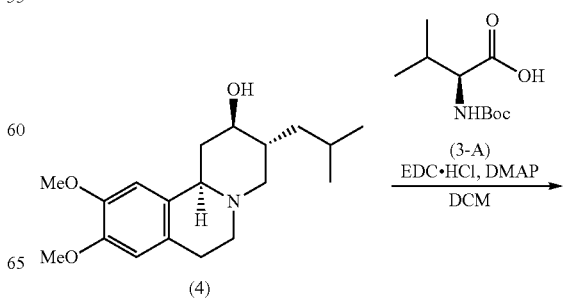

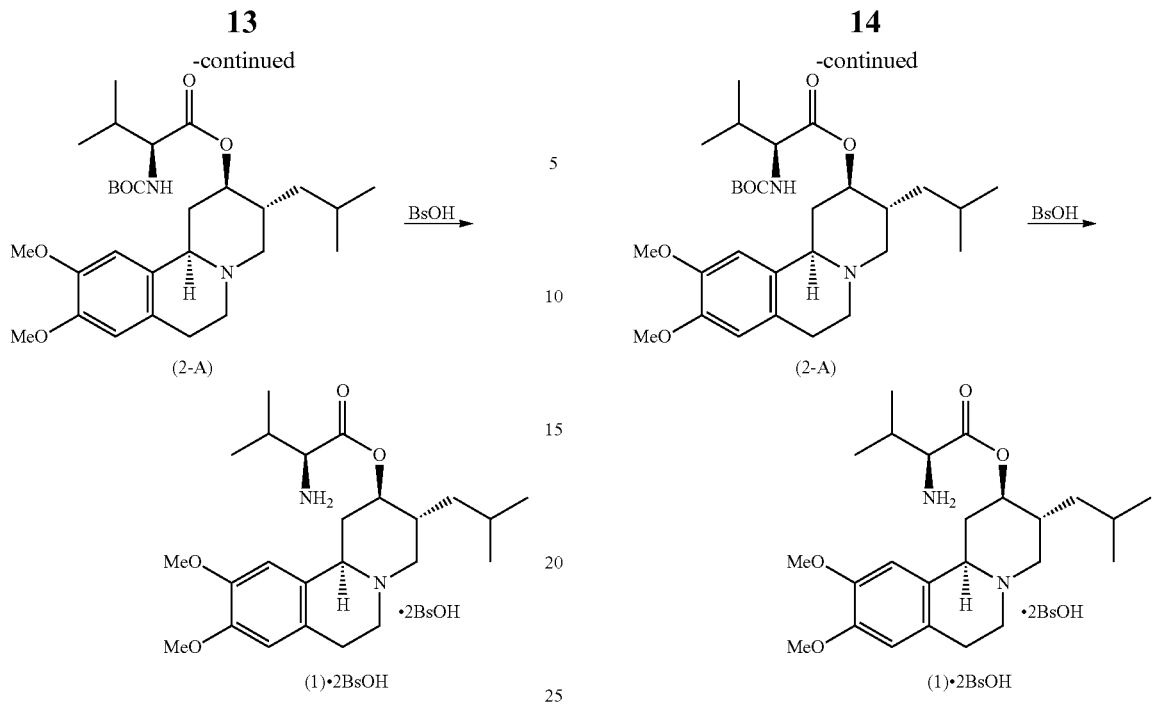

The compound of Formula (3-A) (4.4 g, 0.020 mol) and 4-(dimethylamino)pyridine (DMAP) (0.19 g) were added to a solution of the compound of Formula (4) (5 g, 0.016 mol) in dichloromethane (60 mL) at 0-5° C., followed by the addition of N-(3-dimethylaminopropyl)-W-ethylcarbodiimide hydrochloride (EDC•HCl) (3.9 g, 0.020 mol). The resulting mixture was stirred at 0-5° C. until reaction completion (as determined by thin-layer chromatography (TLC)), whereupon water (50 mL) was added and the layers were separated. The organic layer was washed with water (30 mL) and distilled to low volume in vacuo by rotary evaporation. Acetonitrile (50 mL) was added to the resulting residue of the compound of Formula (2-A), followed by benzenesulfonic acid (4.95 g, 0.031 mol). The resulting clear, yellow solution was stirred at room temperature for approximately 18 hours. Following completion of the deprotection (as determined by TLC), the resulting clear solution was concentrated nearly to dryness in vacuo on a rotary evaporator. Acetone (25 mL) was added to the residue to afford a clear solution, which, following stirring for approximately 2 hours afforded a light yellow precipitate. Filtration and drying in vacuo at 45-50° C. for approximately 18 hours afforded Valbenazine dibesylate Form APO-I (7.35 g, 64% yield, 98% purity by HPLC). The PXRD diffractogram and DSC thermogram of a sample prepared by this method are provided in FIG. 1 and FIG. 2, respectively.

Example 2: Preparation of Valbenazine Dibesylate Form APO-I

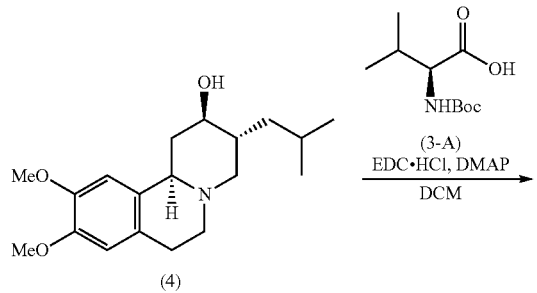

The compound of Formula (3-A) (27.11 g, 0.125 mol) and DMAP (1.30 g) were added to a solution of the compound of Formula (4) (35.0 g, 0.104 mol) in dichloromethane (350 mL) at 0-5° C. followed by the portion-wise addition of EDC•HCl (24.0 g, 0.125 mol). The resulting mixture was stirred at 0-5° C. until reaction completion as determined by TLC, whereupon water (175 mL) was added to the reaction mixture and the layers were separated. Following washing with water (175 mL), the separated organic layer was treated with benzenesulfonic acid (38.0 g, 0.239 mol). The resulting clear, yellow solution was heated to approximately 35-40° C. and maintained for approximately six hours. After reaction completion as determined by TLC, butanone (350 mL) was slowly added and the resulting suspension was heated to 50-55° C. Following stirring at this temperature for approximately five hours, the solid was collected by filtration, washed with butanone (70 mL) and dried in vacuo at 45-50° C. for approximately 18 hours to afford Valbenazine dibesylate Form APO-I (65.31 g, 85.5% yield, 99% purity by HPLC) having a PXRD consistent with FIG. 1.

Example 3: Comparative Solubility of Valbenazine Forms

The solubility of Valbenazine free base, Valbenazine ditosylate and Valbenazine dibesylate were measured in buffer solutions (pH 1.2 to 6.8) in a temperature-controlled water bath at 37° C. with stirring using magnetic stir bars at 325 rpm (rotations per minute). Each Valbenazine sample was weighed and transferred into a 20 mL vial and then 10 mL of buffer was added. The samples were shaken for 1 minute. If all sample dissolved, more sample was added until a saturated solution was obtained. The samples were then equilibrated at 37° C. with stirring using magnetic stir bars at 325 rpm for 24 hours. After equilibration, samples were filtered through 0.45 μm PVDF filters and further diluted with a methanol/water (60/40 v/v) solution. Samples were analyzed by HPLC against known concentrations of standards. The pH values of the solutions were measured after completion of testing. The testing results are summarized in Table 2.

TABLE 2

Solubility of Valbenazine Forms at Variable pH

| Buffer | Valbenazine Form | Final pH (after adjustment) | Solubility expressed as Valbenazine free base (mg/mL) |
|---|---|---|---|
| pH 1.2 | Ditosylate salt | 1.216 | 20.9 |
|  | Dibesylate salt | 1.228 | 22.4 |
|  | Free base | 1.252 | 21.3 |
| pH 4.5 | Ditosylate salt | 4.613 | 17.7 |
|  | Dibesylate salt | 4.513 | 18.5 |
|  | Free base | 4.528 | 21.6 |
| pH 6.8 | Ditosylate salt | 6.771 | 7.6 |
|  | Dibesylate salt | 6.835 | 8.1 |
|  | Free base | 6.801 | 1.2 |

What is claimed is:

1. A crystalline form of Valbenazine dibesylate characterized by a PXRD diffractogram comprising peaks, expressed in degrees 2θ (±0.2°), at 6.3°, 9.8° and 15.6°.

2. The crystalline form of claim 1, characterized by a PXRD diffractogram further comprising at least three peaks, expressed in degrees 2θ (±0.2°), selected from the group consisting of: 5.3°, 7.7°, 8.5°, 12.5°, 14.0°, 16.8°, 17.1°, 17.8°, 18.6° and 19.7°.

3. The crystalline form of claim 1, characterized by a PXRD diffractogram further comprising peaks, expressed in degrees 2θ (±0.2°), at 5.3°, 7.7°, 8.5°, 12.5°, 14.0°, 16.8°, 17.1°, 17.8°, 18.6° and 19.7°.

4. The crystalline form of claim 1, characterized by a DSC thermogram comprising an endothermic peak with a peak onset of approximately 235° C. and a peak maximum of approximately 238° C.

5. The crystalline form of claim 1, characterized by a DSC thermogram that is substantially the same in appearance as the DSC thermogram provided in FIG. 2.

6. The crystalline form of claim 1, providing a PXRD diffractogram comprising peaks in substantially the same positions (±0.2° 2θ) as those shown in FIG. 1.

7. A pharmaceutical composition comprising the crystalline form of Valbenazine dibesylate according to claim 2, and one or more pharmaceutically acceptable excipients.

8. The pharmaceutical composition of claim 7, wherein the pharmaceutical composition is a capsule.

9. The pharmaceutical composition of claim 7, wherein the pharmaceutical composition comprises an amount of the crystalline form that is equivalent to 40 mg or 80 mg Valbenazine free base.

10. A process for the preparation of the crystalline form of Valbenazine dibesylate according to claim 1, the process comprising:

(i) reacting, in the presence of a first solvent (S1), a compound of Formula (2):

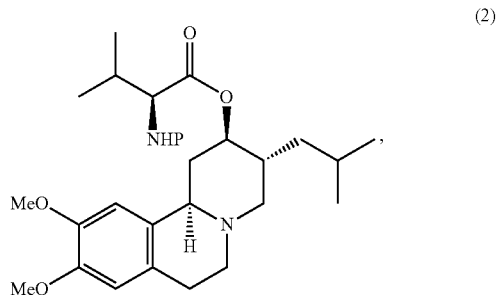

with at least two equivalents of benzenesulfonic acid to afford Valbenazine dibesylate;

(ii) forming a suspension by crystallization of the Valbenazine dibesylate; and (iii) filtering the suspension to isolate the crystalline Valbenazine dibesylate, wherein P is an acid-labile protecting group, wherein P is tert-butoxycarbonyl.

11. The process of claim 10, wherein the first solvent (S1) is selected from the group consisting of nitriles and halogenated hydrocarbons.

12. The process of claim 11, wherein the first solvent (S1) is acetonitrile or dichloromethane.

13. The process of claim 10, wherein the suspension of crystalline Valbenazine dibesylate in step (ii) is formed by the addition of a second solvent (S2).

14. The process of claim 13, wherein the second solvent (S2) is butanone.

15. The process of claim 13, wherein the first solvent (S1) is partially or wholly removed prior to addition of the second solvent (S2).

16. The crystalline form of claim 2, characterized by a DSC thermogram comprising an endothermic peak with a peak onset of approximately 235° C. and a peak maximum of approximately 238° C.

17. The crystalline form of claim 2, characterized by a DSC thermogram that is substantially the same in appearance as the DSC thermogram provided in FIG. 2.

18. The crystalline form of claim 5, providing a PXRD diffractogram comprising peaks in substantially the same positions (±0.2° 2θ) as those shown in FIG. 1.

* * * * *